United States Patent
Gysling

(10) Patent No.: US 7,454,981 B2
(45) Date of Patent: *Nov. 25, 2008

(54) APPARATUS AND METHOD FOR DETERMINING A PARAMETER IN A WET GAS FLOW

(75) Inventor: Daniel L. Gysling, Glastonbury, CT (US)

(73) Assignee: Expro Meters. Inc., Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/749,632

(22) Filed: May 16, 2007

(65) Prior Publication Data

US 2007/0294039 A1    Dec. 20, 2007

Related U.S. Application Data

(60) Provisional application No. 60/801,191, filed on May 16, 2006.

(51) Int. Cl.
*G01F 1/32* (2006.01)
*G01N 9/00* (2006.01)

(52) U.S. Cl. .................................. 73/861.31; 73/32 A
(58) Field of Classification Search ................. 73/32 A, 73/861.31
See application file for complete search history.

(56) References Cited

U.S. PATENT DOCUMENTS

| | | |
|---|---|---|
| 2,874,568 A | 2/1959 | Petermann |
| 4,004,461 A | 1/1977 | Lynworth |
| 4,048,853 A | 9/1977 | Smith et al. |
| 4,080,837 A | 3/1978 | Alexander et al. |
| 4,195,517 A | 4/1980 | Kalinoski et al. |
| 4,248,085 A | 2/1981 | Coulthard |
| 4,445,389 A | 5/1984 | Potzick et al. |
| 4,576,043 A | 3/1986 | Nguyen et al. |
| 4,896,540 A | 1/1990 | Shakkottai et al. |
| 5,040,415 A | 8/1991 | Barkhoudarian |
| 5,083,452 A | 1/1992 | Hope |
| 5,115,670 A | 5/1992 | Shen |

(Continued)

FOREIGN PATENT DOCUMENTS

GB        1 208 121        10/1970

(Continued)

OTHER PUBLICATIONS

"Noise and Vibration Control Engineering Principles and Applications", Leo L. Beranek and Istvan L. Ver, A. Wiley Interscience Publication, pp. 537-541, Aug. 1992.

(Continued)

*Primary Examiner*—Harshad Patel

(57) ABSTRACT

In an apparatus for measuring a parameter of a wet gas flow, a gamma densitometer is provided and configured to non-intrusively measure the density of the wet gas flow. A sonar based flow meter is also provided and configured to non-intrusively determine a flow rate of the gas flow of the wet gas flow. A processing device is in communication with at least one of the gamma densitometer and the sonar based flow meter, the processing device being configured to determine the flow rate of the gas portion and/or liquid portion of the wet gas flow using the measured density and flow rate of the wet gas flow.

17 Claims, 9 Drawing Sheets

U.S. PATENT DOCUMENTS

| | | | |
|---|---|---|---|
| 5,224,372 A | 7/1993 | Kolpak | |
| 5,285,675 A | 2/1994 | Colgate et al. | |
| 5,367,911 A | 11/1994 | Jewell et al. | |
| 5,398,542 A | 3/1995 | Vasbinder | |
| 5,524,475 A | 6/1996 | Kolpak et al. | |
| 5,551,305 A | 9/1996 | Farchi et al. | |
| 5,591,922 A | 1/1997 | Segeral et al. | |
| 5,741,977 A | 4/1998 | Agar et al. | |
| 5,741,980 A | 4/1998 | Hill et al. | |
| 5,770,805 A | 6/1998 | Castel | |
| 5,770,806 A | 6/1998 | Hiismaki | |
| 5,835,884 A | 11/1998 | Brown | |
| 5,856,622 A | 1/1999 | Yamamoto et al. | |
| 5,948,959 A | 9/1999 | Peloquin | |
| 6,151,958 A | 11/2000 | Letton et al. | |
| 6,202,494 B1 | 3/2001 | Riebel et al. | |
| 6,286,360 B1 | 9/2001 | Drzewicki | |
| 6,354,147 B1 | 3/2002 | Gysling et al. | |
| 6,378,357 B1 | 4/2002 | Han et al. | |
| 6,397,683 B1 | 6/2002 | Hagenmeyer et al. | |
| 6,450,037 B1 | 9/2002 | Davis et al. | |
| 6,463,813 B1 | 10/2002 | Gysling et al. | |
| 6,532,827 B1 | 3/2003 | Ohnishi | |
| 6,536,291 B1 | 3/2003 | Gysling et al. | |
| 6,558,036 B2 | 5/2003 | Davis et al. | |
| 6,587,798 B2 | 7/2003 | Gysling et al. | |
| 6,609,069 B2 | 8/2003 | Gysling | |
| 6,691,584 B2 | 2/2004 | Gysling et al. | |
| 6,698,297 B2 | 3/2004 | Gysling | |
| 6,732,575 B2 | 5/2004 | Gysling et al. | |
| 6,782,150 B2 | 8/2004 | Davis et al. | |
| 6,813,962 B2 | 11/2004 | Gysling et al. | |
| 6,837,098 B2 | 1/2005 | Gysling et al. | |
| 6,862,920 B2 | 3/2005 | Gysling et al. | |
| 6,889,562 B2 | 5/2005 | Gysling et al. | |
| 6,898,541 B2 | 5/2005 | Gysling et al. | |
| 6,945,095 B2 | 9/2005 | Johansen | |
| 6,959,604 B2 | 11/2005 | Davis et al. | |
| 6,971,259 B2 | 12/2005 | Gysling | |
| 6,988,411 B2 | 1/2006 | Gysling et al. | |
| 7,032,432 B2 | 4/2006 | Gysling et al. | |
| 7,062,976 B2 | 6/2006 | Gysling et al. | |
| 7,086,278 B2 | 8/2006 | Gysling et al. | |
| 7,096,719 B2 | 8/2006 | Gysling | |
| 7,110,893 B2 | 9/2006 | Davis et al. | |
| 7,127,360 B2 | 10/2006 | Davids et al. | |
| 7,134,320 B2 * | 11/2006 | Gysling et al. | 73/32 A |
| 7,139,667 B2 | 11/2006 | Gysling et al. | |
| 7,343,820 B2 * | 3/2008 | Gysling et al. | 73/861.23 |
| 7,363,800 B2 * | 4/2008 | Gysling | 73/19.01 |
| 2003/0089161 A1 | 5/2003 | Gysling | |
| 2003/0136186 A1 | 7/2003 | Gysling | |
| 2003/0154036 A1 | 8/2003 | Gysling et al. | |
| 2004/0069069 A1 | 4/2004 | Croteau | |
| 2004/0074312 A1 | 4/2004 | Gysling | |
| 2004/0139791 A1 | 7/2004 | Johansen | |
| 2004/0168522 A1 | 9/2004 | Fernald et al. | |
| 2004/0168523 A1 | 9/2004 | Bailey et al. | |
| 2004/0194539 A1 | 10/2004 | Gysling | |
| 2004/0199340 A1 | 10/2004 | Gysling et al. | |
| 2004/0226386 A1 | 11/2004 | Gysling | |
| 2004/0231431 A1 | 11/2004 | Bailey et al. | |
| 2004/0255695 A1 | 12/2004 | Gysling et al. | |
| 2005/0005912 A1 | 1/2005 | Gysling et al. | |
| 2005/0011278 A1 | 1/2005 | Brown et al. | |
| 2005/0011283 A1 | 1/2005 | Gysling et al. | |
| 2005/0012935 A1 | 1/2005 | Kersey | |
| 2005/0039520 A1 | 2/2005 | Bailey et al. | |
| 2005/0044929 A1 | 3/2005 | Banach et al. | |
| 2005/0061060 A1 * | 3/2005 | Gysling et al. | 73/32 A |
| 2005/0120799 A1 | 6/2005 | Gysling et al. | |
| 2005/0125169 A1 | 6/2005 | Loose | |
| 2005/0125170 A1 | 6/2005 | Gysling | |
| 2005/0159904 A1 | 7/2005 | Loose et al. | |
| 2005/0171710 A1 | 8/2005 | Gysling et al. | |
| 2005/0246111 A1 | 11/2005 | Gysling et al. | |
| 2006/0037385 A1 * | 2/2006 | Gysling | 73/61.44 |
| 2006/0037399 A1 | 2/2006 | Brown | |
| 2006/0048583 A1 | 3/2006 | Gysling | |
| 2006/0053809 A1 | 3/2006 | Gysling et al. | |
| 2006/0096388 A1 * | 5/2006 | Gysling et al. | 73/861.03 |
| 2006/0266127 A1 * | 11/2006 | Gysling | 73/861.23 |
| 2007/0005272 A1 * | 1/2007 | Gysling | 702/50 |
| 2007/0044572 A1 * | 3/2007 | Davis et al. | 73/861.42 |
| 2007/0055464 A1 * | 3/2007 | Gysling | 702/50 |
| 2007/0157737 A1 * | 7/2007 | Gysling et al. | 73/861.23 |

FOREIGN PATENT DOCUMENTS

| | | |
|---|---|---|
| GB | 2 282 931 | 4/1995 |
| WO | WO 93/14382 | 7/1993 |
| WO | WO 9301934 | 9/1993 |
| WO | WO 99/67629 | 12/1999 |
| WO | WO 02/46706 | 6/2002 |
| WO | WO 03007304 | 9/2003 |
| WO | WO 2005004073 | 5/2005 |

OTHER PUBLICATIONS

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

Sonar-Based Volumetric Flow Meter for Pulp and Paper Applications—By: Daniel L. Gysling & Douglas H. Loose—Dec. 3, 2002.

Sonar Based Volumetric Flow Meter for Chemical and Petrochemical Applications—By: Daniel L. Gysling & Douglas H. Loose—Feb. 14, 2003.

Clamp-On, Sonar Based Entrained Air Measurement for Pulp and Paper Applications—By: Daniel L. Gysling & Douglas H. Loose—Jan. 24, 2003.

"Flow Velocity Measurement using Spatial Filter" By: Yoshio Kurita, Takaharu Matsumoto and Yukitake Shibata, Nov. 1979.

U.S. Appl. No. 11/115,492, P. Rothman.

U.S. Appl. No. 11/268,815, D. Gysling et al.

"New Flowmeter Principle"—By: Walt Boyes—Published in Flow Control Magazine—Oct. 2003 Issue.

Piezo Film Sensors Technical Manual—Measurement Specialties, Inc. Apr. 2, 1999.

* cited by examiner

APPARATUS AND METHOD FOR DETERMINING A PARAMETER IN A WET GAS FLOW

CROSS-REFERENCE TO RELATED APPLICATION

The present application claims the benefit of U.S. Provisional Patent Application No. 60/801,191 filed May 16, 2006 and is incorporated by reference herein in its entirety.

BACKGROUND OF THE INVENTION

A fluid flow process (flow process) includes any process that involves the flow of fluid through pipes, ducts, or other conduits, as well as through fluid control devices such as pumps, valves, orifices, heat exchangers, and the like. Flow processes are found in many different industries such as the oil and gas industry, refining, food and beverage industry, chemical and petrochemical industry, pulp and paper industry, power generation, pharmaceutical industry, and water and wastewater treatment industry. The fluid within the flow process may be a single phase fluid (e.g., gas, liquid or liquid/liquid mixture) and/or a multi-phase mixture (e.g. paper and pulp slurries or other solid/liquid mixtures). The multi-phase mixture may be a two-phase liquid/gas mixture, a solid/gas mixture or a solid/liquid mixture, or a gas entrained liquid. The fluid may also be a three-phase mixture such as a gas/liquid/liquid mixture or a gas/liquid/solid mixture.

In certain flow processes, such as those found in the oil and gas industries, it is desirable to separate the liquid (e.g., oil and/or water) and the gas (e.g., air) components of the fluid. This is typically accomplished using a separator, which is an item of production equipment used to separate liquid components of the fluid stream from gaseous components. The liquid and gas components flow from the separator in separate legs (pipes), with the leg containing the gas component referred to as the "gas leg" and the leg containing the liquid component referred to as the "liquid leg". Each of the legs typically includes a flow meter to determine the volumetric flow rate for each of the gas and the fluid components, respectively, wherein the volumetric flow rate for the gas leg is commonly measured using an orifice plate.

As is well known in oil and gas production, the carry-over of liquid into the gas leg of the gas/liquid separator commonly occurs, wherein the liquid typically takes the form of a mist comprised of small liquid droplets, commonly known as wet gas. This is undesirable because the liquid carry-over can result in a host of undesirable events depending in large part on the degree of carry-over that takes place. As such, in order to minimize the amount of liquid carry-over most separators have mist catchers designed to recover the liquid carried over. Unfortunately however, accurate measurements of the amount of liquid carry-over have not been obtainable because there currently exists no devices and/or methods for accurately determining the amount of liquid carried over into the gas leg. As such, there is a need for an apparatus and method to accurately measure the amount of liquid carry-over as well as the flow rates of the liquid and gas phases of the wet gas flow.

A difficulty that often occurs when taking measurements relevant to fluid flows within conduits such as pipes results from the fact that it is often necessary to have sensors within the flowing fluid. This increases the potential for difficulties associated with leaks as well as weakening the conduit or pipe. This can be particularly problematic when it is necessary to measure flow characteristics and parameters on existing pipes. It may be difficult to make modifications to such systems.

In addition, it may not be feasible, or be too costly to shut a system down to make these modifications.

Based on the foregoing, it is the general objection of the present invention to provide an apparatus and method for determining wetness in a gas flow that improves upon or overcomes the problems and drawbacks associated with the prior art.

SUMMARY OF THE INVENTION

The present invention resides in one aspect in an apparatus for measuring a parameter of a wet gas flow wherein a gamma densitometer is provided and configured to non-intrusively measure the density of a wet gas flow traveling through a conduit. A sonar based flow meter is also provided and configured to non-intrusively determine a flow rate of the wet gas flow traveling through the conduit. A processing device is in communication with at least one of the gamma densitometer and the sonar based flow meter, and is configured to determine at least the flow rates of the liquid and/or gas phases of the wet gas flow using the measured density and flow rate of the wet gas flow.

The present invention resides in another aspect in a method of measuring a parameter of a wet gas flow wherein the method includes non-intrusively determining a density of the gas flow responsive to changes in radiation transmitted through the wet gas flow. The method further includes non-intrusively determining a volumetric flow rate of the wet gas flow responsive to the unsteady pressures caused by coherent structures convecting with the gas flow. Additionally, the method includes processing the density and the wet gas flow rate to determine at least the flow rate of the liquid and/or gas phases of the wet gas flow.

BRIEF DESCRIPTION OF THE DRAWINGS

Referring now to the drawings, the foregoing and other features and advantages of the present invention will be more fully understood from the following detailed description of illustrative embodiments, taken in conjunction with the accompanying drawings.

DETAILED DESCRIPTION

Figure 1:
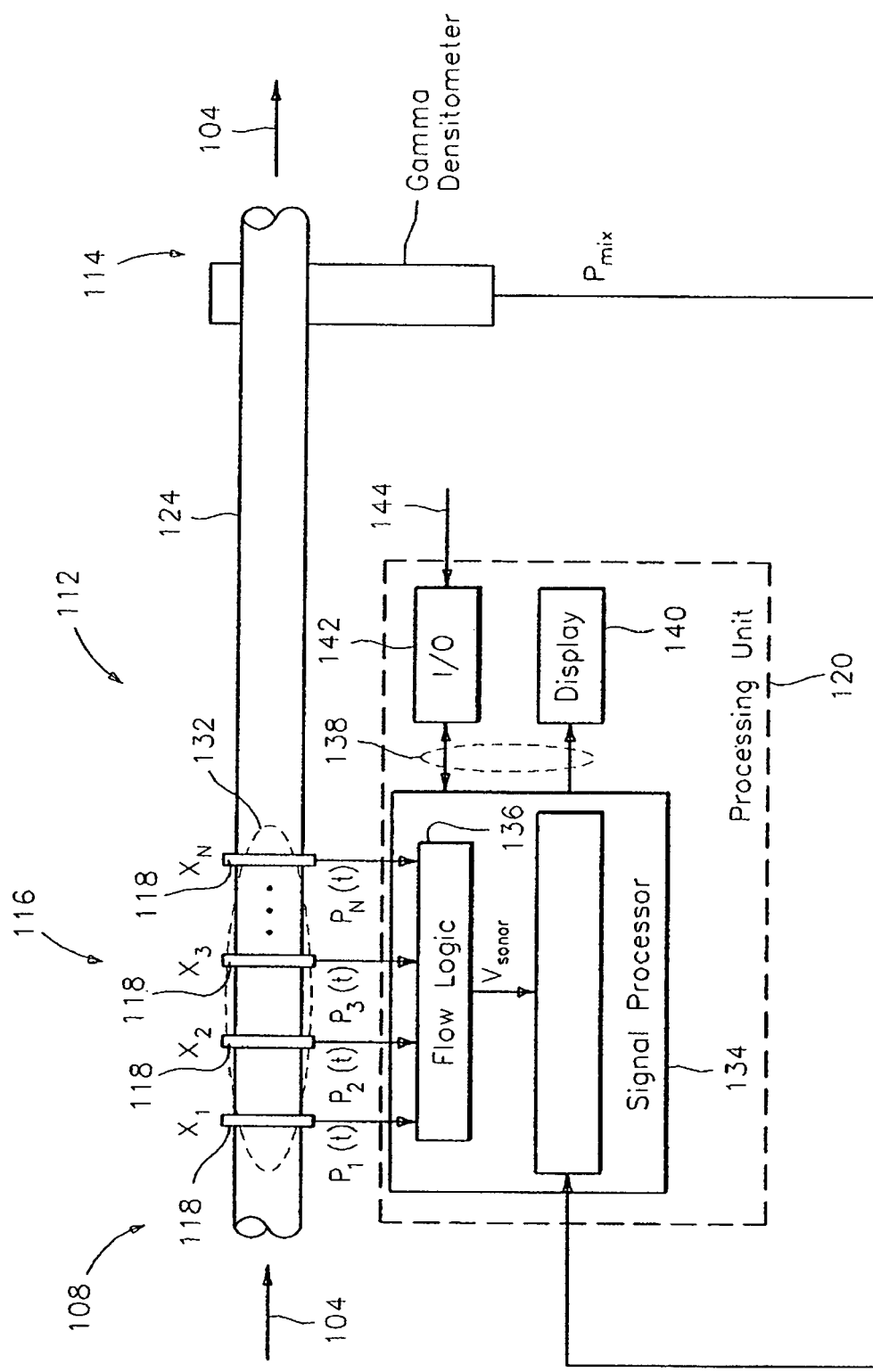
FIG. 1 is a schematic diagram of an embodiment of an apparatus for measuring the wetness of a wet gas flow within a pipe, wherein a flow meter having an array of sensors (sonar meter) is disposed upstream of a gamma densitometer in accordance with the present invention.
Figure 2:
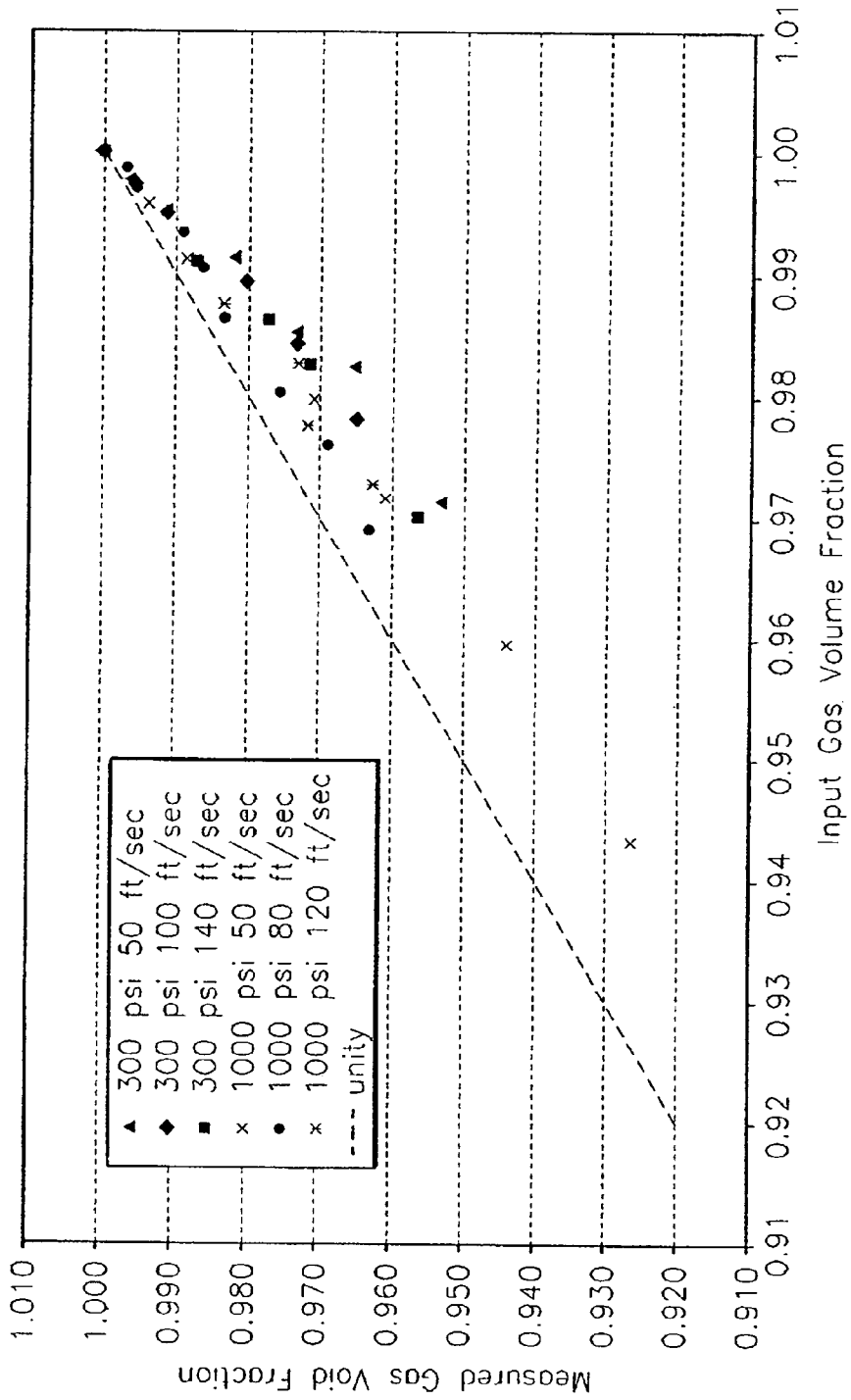
FIG. 2 is a plot showing measured gas void fraction versus input gas volume fraction generated from data obtained using the apparatus of FIG. 1.

As shown in FIG. 1, a schematic diagram of a first embodiment of an apparatus 112 for measuring flow rates of a wet gas flow 104 flowing within a conduit or pipe 124 is shown. The apparatus 112 includes a gamma densitometer 114 and a flow meter 116 having an array of sensors 118 (sonar flow meter). The gamma densitometer 114 and the sonar flow meter 116 are each configured to be coupled to an outer surface of the pipe 124. The gamma densitometer 114, in lieu of being coupled to the outer surface of the pipe 124 can be positioned in operational proximity thereto. The gamma densitometer 114 and the sonar flow meter 118 each operate in a manner that does not require any mechanical intrusion through the pipe and into the fluid flow. As such, the sonar flow meter 116 and the gamma densitometer 114 are each non-intrusive, non-contact (non-wetted) sensors.

In use, the gamma densitometer 114 and the sonar based flow meter 116 can each be clamped onto the pipe 124. In this manner the sonar-based flow meter 116 and the gamma densitometer 114 can be readily positioned for operation on pipes during manufacture or assembly of a new system and are also readily positioned onto existing systems.

In operation the gamma densitometer 114 transmits radiation through the pipe or conduit 124 and the wet gas flow 104 coursing therethrough to measure a mixture density ($\rho_{mix}$) of the wet gas flow. This is accomplished by monitoring changes in the amount of radiation detected after passing through the fluid flow 104.

Similarly, the sonar flow meter 116 determines the flow rate ($V_{sonar}$) of the wet gas flow 104, which will be described in greater detail herein after, and similar to that described in U.S. patent application Ser. No. 10/712,818, filed on Nov. 12, 2003 and U.S. Pat. No. 6,691,584 issued Jul. 2, 1999, which are incorporated herein by reference in their entirety. A processing unit 120, in response to the mixture density ($\rho_{mix}$) provided by the gamma densitometer 114 and the flow rate ($V_{sonar}$) as determined by the sonar flow meter 116, determines at least the liquid and/or gas flow rates of the wet gas flow 104 within the pipe 124.

In the illustrated embodiment, the sonar flow meter 116 is disposed downstream of the gamma densitometer 114. However, it is contemplated by the present invention that the gamma densitometer may be disposed downstream of the sonar flow meter.

The sonar based flow meter 116 includes a spatial array 132 of at least two pressure sensors 118 disposed at different axial locations $x_1 \ldots x_N$ along the pipe 124. Each of the pressure sensors 118 provides a pressure signal P(t) indicative of unsteady pressure within the pipe 124 at a corresponding axial location $x_1 \ldots x_N$ of the pipe 124. A signal processor 134 receives the pressure signals $P_1(t) \ldots P_N(t)$ from the pressure sensors 118 in the array 132, and determines the velocity and volumetric flow rate of the wet gas flow 104 using pressure signals from the pressure sensors 118. The signal processor 134 then applies array-processing techniques to the pressure signals $P_1(t) \ldots P_N(t)$ to determine the velocity, volumetric flow rate, and/or other parameters of the wet gas flow 104.

While the sonar based flow meter 116 is shown as including four pressure sensors 118, it is contemplated that the array 132 of pressure sensors 118 may include two or more pressure sensors 118, each providing a pressure signal P(t) indicative of unsteady pressure within the pipe 124 at a corresponding axial location X of the pipe 124. For example, the sonar based flow meter 116 may include 2, 3, 4, 5, 6, 7, 8, 9, 10, 11, 12, 13, 14, 15, 16, 17, 18, 19, 20, 21, 22, 23, or 24 pressure sensors 118. Generally, the accuracy of the measurement improves as the number of sensors 118 in the array 132 increases. The degree of accuracy provided by the greater number of sensors 118 is offset by the increase in complexity and time for computing the desired output parameter of the flow. Therefore, the number of sensors 118 used is dependent at least on the degree of accuracy desired and the desired update rate of the output parameter provided by the meter 116.

The signals $P_1(t) \ldots P_N(t)$ provided by the pressure sensors 118 in the array 132 are processed by the signal processor 134, which may be part of the larger processing unit 120. For example, the signal processor 134 may be a microprocessor and the processing unit 120 may be a personal computer or other general purpose computer. It is contemplated that the signal processor 134 may be any one or more analog or digital signal processing devices for executing programmed instructions, such as one or more microprocessors or application specific integrated circuits (ASICS), and may include memory for storing programmed instructions, set points, parameters, and for buffering or otherwise storing data. Further, it should be appreciated that some or all of the functions within the flow logic 136 may be implemented in software (using a microprocessor or computer) and/or firmware, or may be implemented using analog and/or digital hardware, having sufficient memory, interfaces, and capacity to perform the functions described herein.

To determine the flow rate $V_{sonar}$ of the wet gas flow 104, the signal processor 134 applies the data from the pressure sensors 118 to flow logic 136 executed by the signal processor 134. It is also contemplated that the signal processor 134 will receive and manipulate signals generated by the gamma densitometer 114 indicative of the mixture density of the wet gas flow 104. Using the mixture density of the wet gas flow 104 determined by the gamma densitometer 114 ($\rho_{mix}$) and the flow rate of the wet gas flow 104 determined by the sonar based flow meter 116 ($V_{sonar}$), the signal processor 134 can determine the flow rates (or superficial velocities) of the liquid and gas phases, $V_{sliq}$ and $V_{sgas}$ respectively in the wet gas flow 104 using the following equations.

$$\rho_{mix} = \alpha_{liq}\rho_{liq} + \alpha_{gas}\rho_{gas} \qquad \text{Equation 1}$$

Where $\rho_{mix}$ is the density of the wet gas flow as measured by the gamma densitometer, $\alpha_{liq}$ is liquid hold-up of the wet gas flow 104, $\rho_{liq}$ is density of a liquid phase of the wet gas flow, $\alpha_{gas}$ is gas hold-up of the wet gas flow, and $\rho_{gas}$ is the density of the gas phase of the wet gas flow. Liquid hold-up $\alpha_{liq}$ is an indication of the fraction of the conduit or pipe that is occupied by liquid, and is directly related to the wetness of the wet gas flow 104.

$$1 = \alpha_{liq} + \alpha_{gas} \qquad \text{Equation 2}$$

$$1 = \emptyset_{gas} + \emptyset_{liq} \qquad \text{Equation 3}$$

Where $\emptyset_{gas}$ is the gas volume fraction of the wet gas mixture, and $\emptyset_{liq}$ is the liquid volume fraction of the wet gas mixture.

$$\emptyset_{liq} = \frac{\alpha_{liq}}{1-M} \quad \text{Equation 4}$$

Where M is empirically derived and is governed by the equation:

$$M = 0.79 + 0.41 Fr \quad \text{Equation 5}$$

Where Fr is the Froude Number.

Sonar meters are relatively insensitive to wetness, however, the insensitivity of a sonar meter to wetness deteriorates with decreasing densimetric Froude numbers (Fr), wherein the densimetric Froude number is a measure of the degree of "mixedness" in the flow. As is known, the Froude number is given by, $$Fr \equiv \left(\sqrt{\frac{\rho_{gas}}{\rho_{liq}-\rho_{gas}}}\right) \frac{V_{Sonar}}{\sqrt{gD}} \quad \text{Equation 6}$$

Wherein $V_{sonar}$ is the flow rate of the wet gas as measured by the sonar flow meter, Fr is the Froude number and is determined using the sonar meter, $\rho_{gas}$ is the gas density, $\rho_{liq}$ is the liquid density and gD is the force of gravity multiplied by the inner diameter of the pipe. It should be appreciated that flows that are well mixed provide better results than flows that are not well mixed. As such, because the Froude Number is indicative of the well-ness of the mixture (i.e. the higher the Froude number, the better the flow is mixed), a flow having a Froude Number that is equal to or greater than 2 tends to allow for optimal results. For example, for a Froude number of greater than 2 (i.e. Fr>2), the reported gas rates from the sonar meter are typically within 5% of the actual amount, independent of wetness.

$$V_{sliq} = V_{sonar} \emptyset_{liq} \quad \text{Equation 7}$$

$$V_{sgas} = V_{sonar} \emptyset_{gas} \quad \text{Equation 8}$$

In applying the equations set forth above, the mixture density ($\rho_{mix}$) is measured by the gamma densitometer. The liquid density ($\rho_{liq}$) and the gas density ($\rho_{gas}$) are known. Equation 2 can be solved for $\alpha_{liq}$ so that $\alpha_{liq} = 1 - \alpha_{gas}$. This can then be substituted into Equation 1 above and the liquid hold-up $\alpha_{liq}$ can be solved for. The Froude number Fr can be determined from equation 6 and then Equation 5 can be solved for M. Knowing M and $\alpha_{liq}$ allows the volume fraction of the liquid $\phi_{liq}$ to be solved for in accordance with Equation 4. Once $\emptyset_{liq}$ is known, $\emptyset_{gas}$ can be determined using Equation 3. Knowing $\emptyset_{liq}$ and $\emptyset_{gas}$, the superficial velocity of the gas portion and liquid portion ($Vs_{liq}$ and $Vs_{gas}$) are easily determined employing Equations 7 and 8. Further knowing the cross-sectional area of the inner portion of the pipe conduit (A), the volumetric flow rate of each of the gas portion and liquid portion ($Q_{liq}$, $Q_{gas}$) may be determined by the following equations:

$$Q_{gas} = Vs_{gas} A \quad \text{Equation 9}$$

$$Q_{liq} = Vs_{liq} A \quad \text{Equation 10}$$

Figure 3:
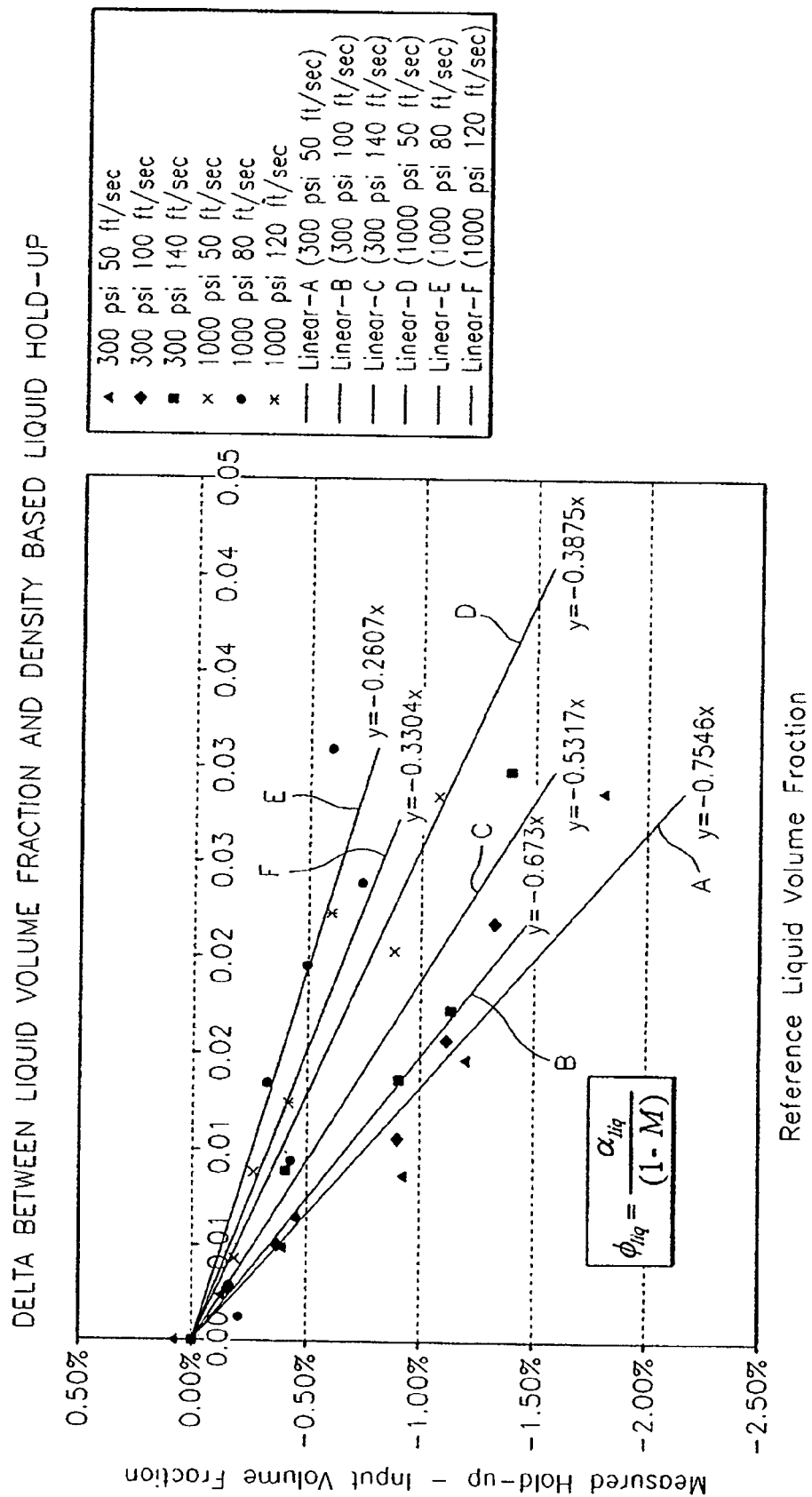
FIG. 3 is a plot showing the delta between liquid volume fraction and density based liquid hold up generated from data obtained using the apparatus of FIG. 1.
Figure 4:
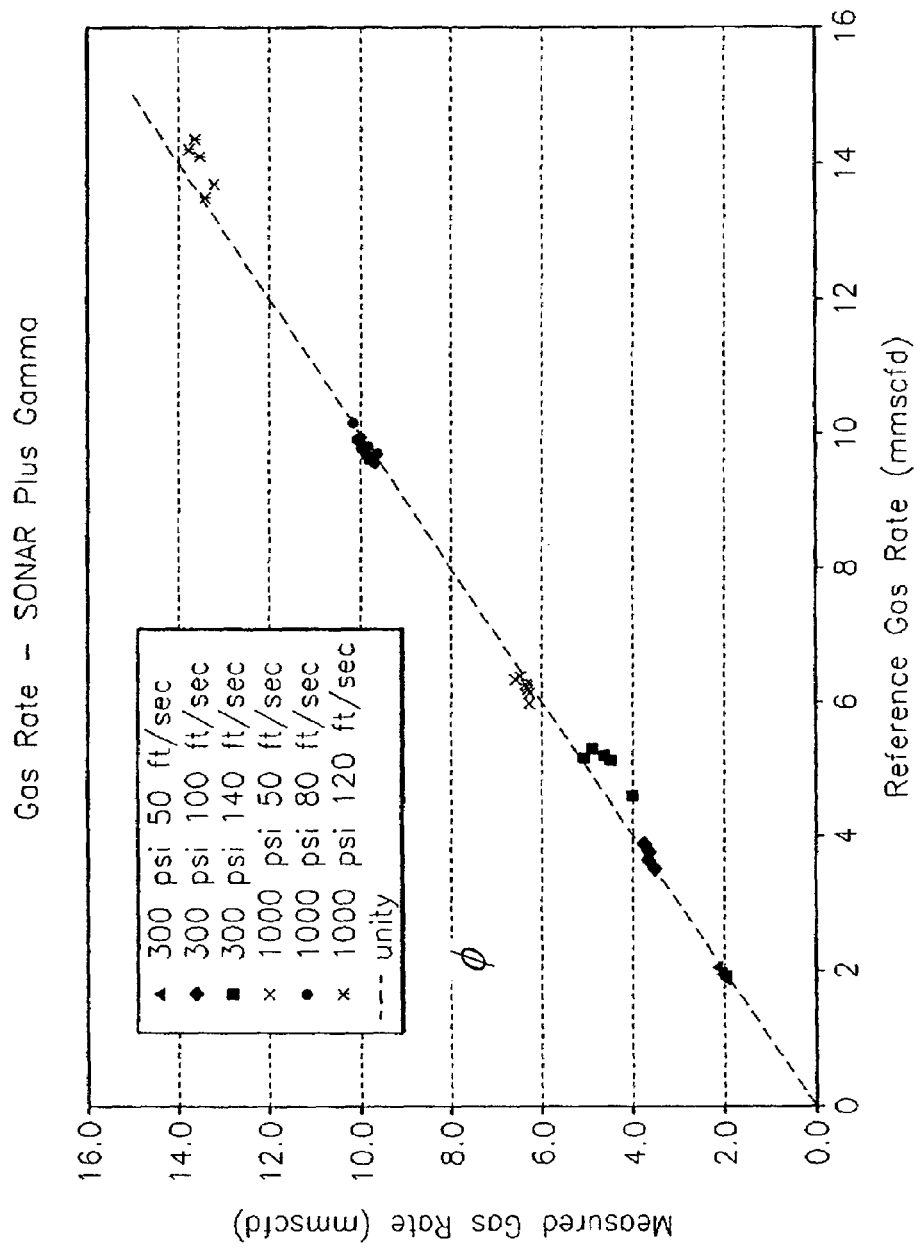
FIG. 4 is a plot showing measured gas rate versus reference gas rate generated from data obtained using the apparatus of FIG. 1.
Figure 5:
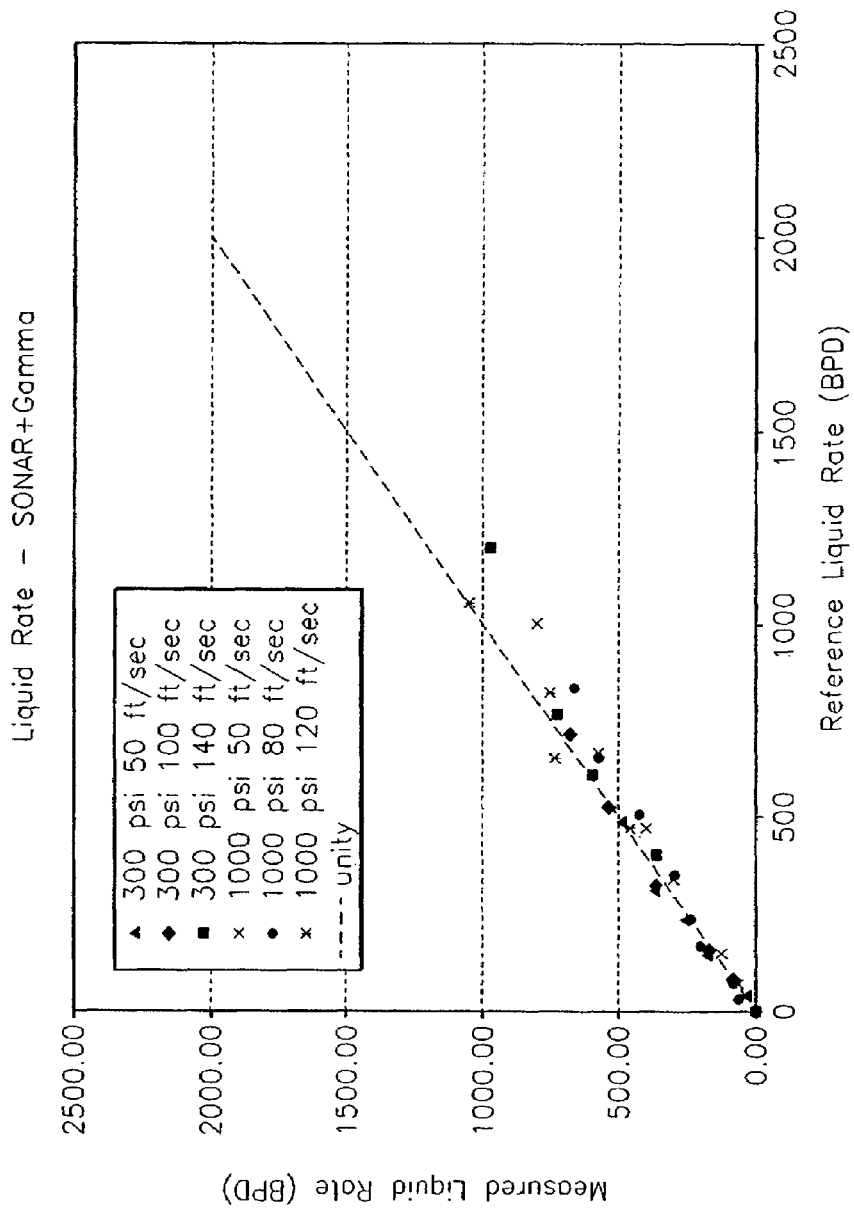
FIG. 5 is a plot showing measured liquid rate versus reference liquid rate generated from data obtained using the apparatus of FIG. 1.
Figure 6:
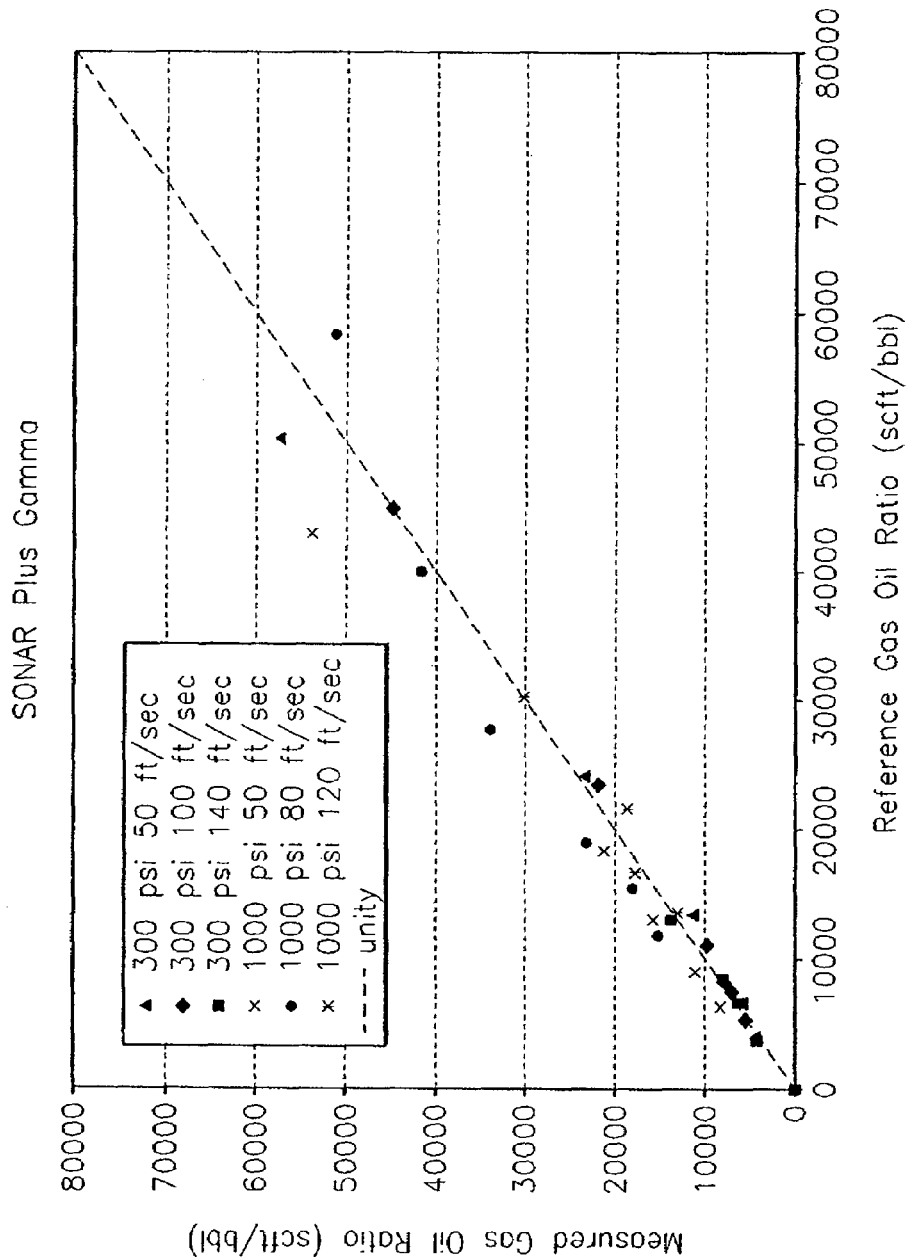
FIG. 6 is a plot showing measured gas oil ratio versus reference gas oil ratio generated from data obtained using the apparatus of FIG. 1.

FIGS. 2-6 illustrate various parameters measured using the sonar flow meter 116 and the gamma densitometer 114 of the present invention. FIG. 3 is illustrative of the liquid phase volume fraction determined by employing Equation 3, set forth above.

While the description for the sonar meter 116 provides an output signal representative of the velocity or flow rate of the wet gas to be used in the determination of the flow rates of the liquid and gas phases, the invention contemplates that any other output of the sonar meter 116, which is insensitive to wetness may be used in determining the wetness of the wet gas flow 104.

The signal processor 134 may output the flow rates and/or the wetness of the wet gas flow 104, as well as various other parameters that may be determined, as a signal 138. The signal 138 may be provided to a display 140, another input/output (I/O) device 142 or another processing device for further processing. Moreover, the I/O device 142 may also accept user input parameters 144 as may be necessary for the flow logic 136. The I/O device 142, display 140, and/or signal processor unit 134 may be mounted in a common housing, which may be attached to the array 132 by a flexible cable, wireless connection, or the like. The flexible cable may also be used to provide operating power from the processing unit 120 to the array 132 if necessary. The signal processor 134 may also produce an output signal that can be used, under certain conditions, to control other devices, such as, but not limited to, pumps and valves, as well as, provide an alarm or indicator when certain conditions are met.

It should be appreciated that the sonar meter 116 may comprise a plurality of ultrasonic sensors 118 to provide an output signal, for example a velocity measurement. The ultrasonic sonar flow meter 116 is similar to that described in U.S. patent application Ser. No. 10/756,977 filed on Jan. 13, 2004 and U.S. patent application Ser. No. 10/964,043 filed on Oct. 12, 2004, which are incorporated herein by reference.

It should be further appreciated that the sensors 118 may also include electrical strain gages, optical fibers and/or gratings, ported sensors, among others as described herein, and may be attached to the pipe 124 by adhesive, glue, epoxy, tape or other suitable attachment means to ensure suitable contact between the sensor and the pipe 124. Additionally, the sensors 118 may alternatively be removable or permanently attached via known mechanical techniques such as mechanical fastener, spring loaded, clamped, clam shell arrangement, strapping or other equivalents. Alternatively, strain gages, including optical fibers and/or gratings, may be embedded in a composite pipe 124. If desired, for certain applications, gratings may be detached from (or strain or acoustically isolated from) the pipe 124 if desired. It is also contemplated that any other strain sensing technique may be used to measure the variations in strain in the pipe 124, such as highly sensitive piezoelectric, electronic or electric, strain gages attached to or embedded in the pipe 124.

In various embodiments of the present invention, a piezoelectric pressure transducer may be used as one or more of the pressure sensors 118 and it may measure the unsteady (or dynamic or ac) pressure variations inside the pipe 124 by measuring the pressure levels inside the pipe 124. In one embodiment of the present invention, the sensors 118 comprise pressure sensors manufactured by PCB Piezotronics of Depew, N.Y. For example, in one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi). The sensors 118 may incorporate a built-in MOSFET microelectronic amplifier to convert the high-impedance charge output into a low-impedance voltage signal. The sensors 118 may be powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves. The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Furthermore it is contemplated that each of the sensors 118 may include a piezoelectric sensor that provides a piezoelectric material to measure the unsteady pressures of the flow 104. The piezoelectric material, such as the polymer, polarized fluoropolymer, PVDF, measures the strain induced within the process pipe 124 due to unsteady pressure variations within the flow 104. Strain within the pipe 124 is transduced to an output voltage or current by the attached piezoelectric sensors 118.

The PVDF material forming each piezoelectric sensor 118 may be adhered to the outer surface of a steel strap that extends around and clamps onto the outer surface of the pipe 124. The piezoelectric sensing element is typically conformal to allow complete or nearly complete circumferential measurement of induced strain. The sensors can be formed from PVDF films, co-polymer films, or flexible PZT sensors, similar to that described in "Piezo Film Sensors technical Manual" provided by Measurement Specialties, Inc. of Fairfield, N.J., which is incorporated herein by reference. The advantages of this technique are the following:

1. Non-intrusive flow rate measurements;
2. Low cost;
3. Measurement technique requires no excitation source. Ambient flow noise is used as a source;
4. Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vertical noise detection, d) tailored sensor geometries to minimize sensitivity to pipe modes, e) differencing of sensors to eliminate acoustic noise from vertical signals; and
5. Higher Temperatures (140 C) (co-polymers).

Velocity Processing

As described in commonly-owned U.S. Pat. No. 6,609,069 to Gysling, entitled "Method and Apparatus for Determining the Flow Velocity Within a Pipe", which is incorporated herein by reference in its entirety, the unsteady pressures along a pipe 124 caused by coherent structures (e.g., turbulent eddies and vertical disturbances) that convect with a fluid (e.g., gas flow 104) flowing in the pipe 124, contain useful information regarding parameters of the fluid.

Figure 7:
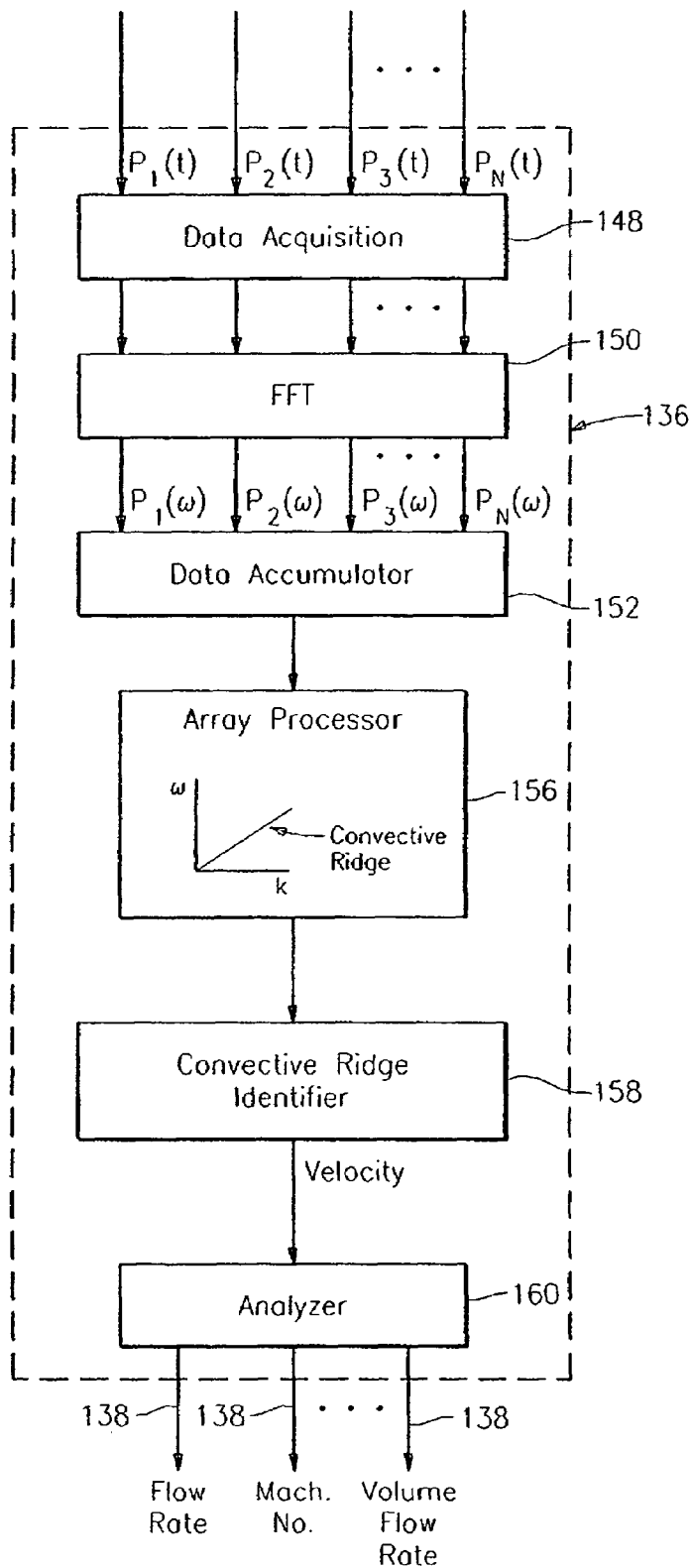
FIG. 7 is a block diagram of a first embodiment of a flow logic for the sonar flow meter in the apparatus of FIG. 1.
Figure 8:
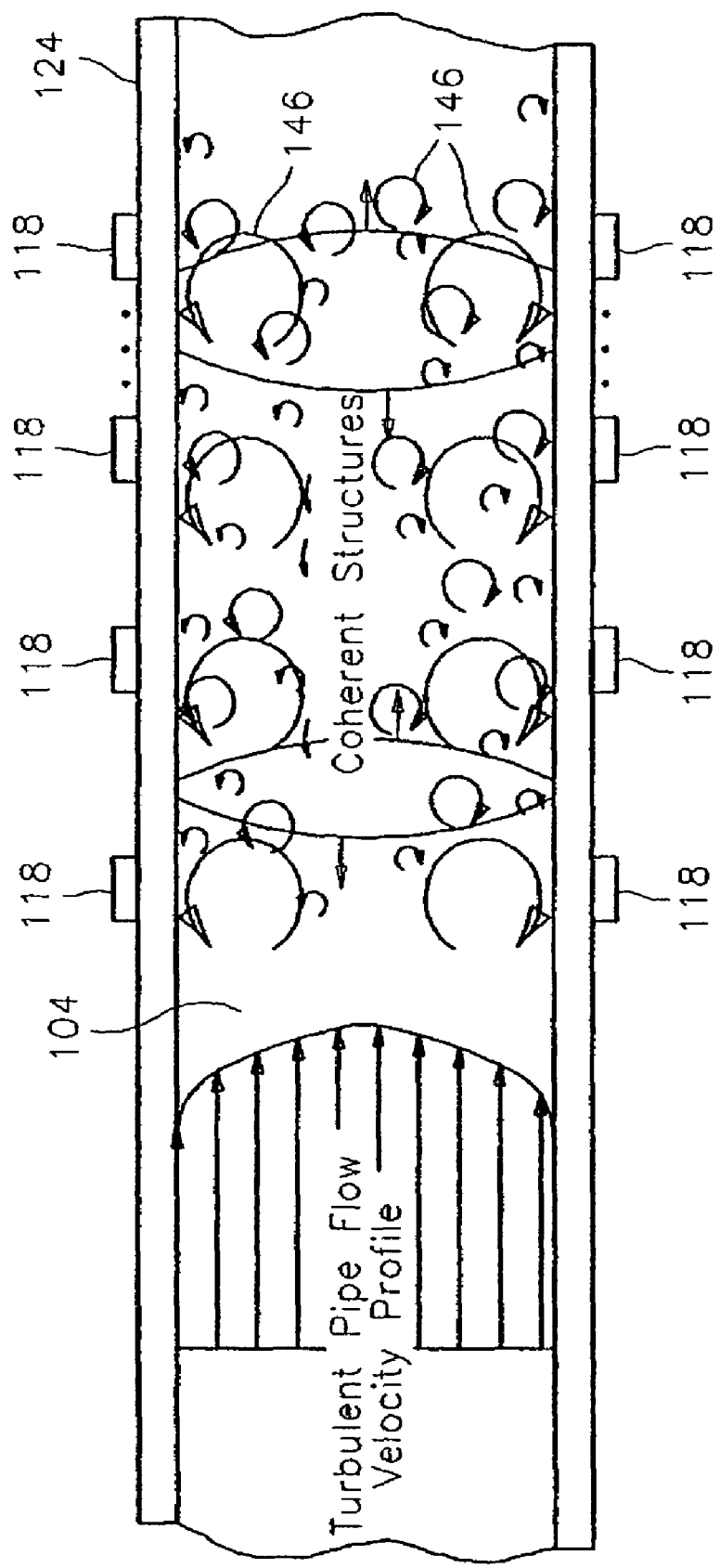
FIG. 8 is a cross-sectional view of a pipe having coherent structures therein.

Referring to FIG. 7, an example of the flow logic 136 is shown. As previously described, the array 132 of at least two sensors 118 located at two locations $x_1$, $x_2$ axially along the pipe 124 sense respective stochastic signals propagating between the sensors 118 within the pipe 124 at their respective locations. Each sensor 118 provides a signal indicating an unsteady pressure at the location of each sensor 118, at each instant in a series of sampling instants. One will appreciate that the array 132 may include more than two sensors 118 distributed at locations $x_1 \ldots x_N$. The pressure generated by the convective pressure disturbances (e.g., eddies 146, see FIG. 8) may be measured through the sensors 118, which may be strained-based sensors and/or pressure sensors. The sensors 118 provide analog pressure time-varying signals $P_1(t)$, $P_2(t), P_3(t) \ldots P_N(t)$ to the signal processor 134, which in turn applies these signals $P_1(t)$, $P_2(t)$, $P_3(t) \ldots P_N(t)$ to the flow logic 136. The flow logic 136 processes the signals $P_1(t)$, $P_2(t), P_3(t) \ldots P_N(t)$ to first provide output signals (parameters) indicative of the pressure disturbances that convect with the fluid (gas) 104, and subsequently, provide output signals in response to pressure disturbances generated by convective waves propagating through the fluid 104, such as velocity, Mach number and volumetric flow rate of the fluid 104.

The signal processor 134 includes data acquisition unit 148 (e.g., A/D converter) that converts the analog signals $P_1(t) \ldots P_N(t)$ to respective digital signals and provides the digital signals $P_1(t) \ldots P_N(t)$ to FFT logic 150. The FFT logic 150 calculates the Fourier transform of the digitized time-based input signals $P_1(t) \ldots P_N(t)$ and provides complex frequency domain (or frequency based) signals $P_1(\omega), P_2(\omega), P_3(\omega), \ldots P_N(\omega)$ indicative of the frequency content of the input signals to a data accumulator 152. Instead of FFTs, any other technique for obtaining the frequency domain characteristics of the signals $P_1(t)$-$P_N(t)$, may also be used. For example, the cross-spectral density and the power spectral density may be used to form one or more frequency domain transfer functions (or frequency responses or ratios) discussed hereinafter. One technique of determining the convection velocity of the turbulent eddies 146 within the fluid 104 is by characterizing a convective ridge (154 in FIG. 9) of the resulting unsteady pressures using an array of sensors or other beam forming techniques, similar to that described in U.S. Pat. No. 6,889,562 and U.S. Pat. No. 6,609,069, which are incorporated herein by reference.

Figure 9:
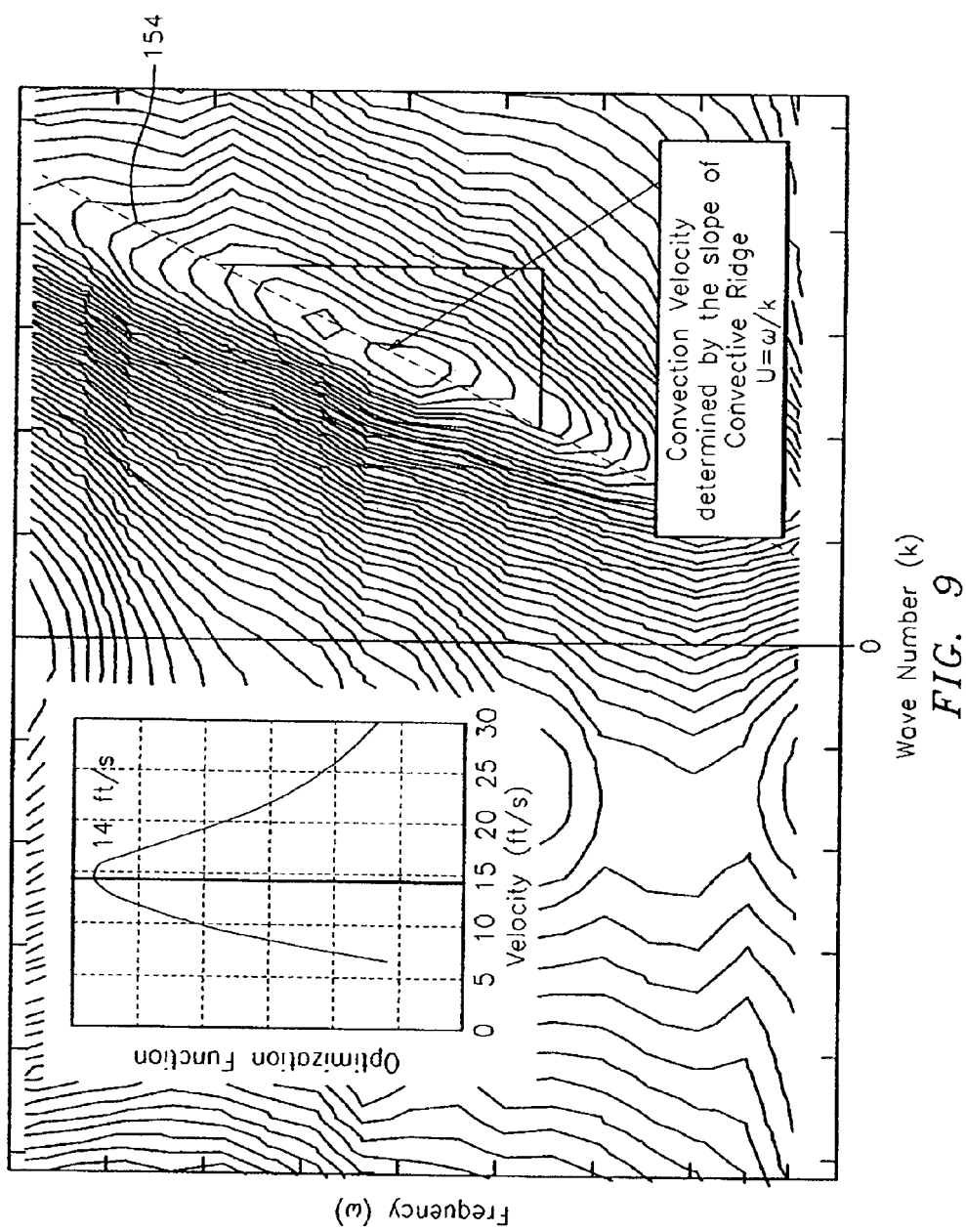
FIG. 9 is a kω plot of data processed from the apparatus of the present invention that illustrates the slope of the convective ridge, and a plot of the optimization function of the convective ridge in accordance with the present invention.

The data accumulator 152 accumulates the frequency signals $P_1(\omega)$-$P_N(\omega)$ over a sampling interval, and provides the data to an array processor 156, which performs a spatial-temporal (two-dimensional) transform of the sensor data, from the xt domain to the k-ω domain, and then calculates the power in the k-ω plane, as represented by the k-ω plot shown in FIG. 9. The array processor 156 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

It should be appreciated that the prior art teaches many algorithms for use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length. Convective characteristics or parameters have a dispersion relationship that can be approximated by the straight-line equation, $$k=\omega/u,\qquad\text{Equation 9}$$

where u is the convection velocity (flow velocity). A plot of k-ω pairs is obtained from a spectral analysis of sensor samples associated with convective parameters. The pairings are portrayed so that the energy of the disturbance spectrally corresponding to the pairings can be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 146 are distributed over a range of length scales and hence temporal frequencies.

To calculate the power in the k-ω plane, as represented by a k-ω plot (see FIG. 9) of either one of the signals, the array processor 156 determines the wavelength and so the (spatial) wave number k, and also the (temporal) frequency and so the angular frequency ω, of various of the spectral components of the stochastic parameter. There are numerous algorithms available in the public domain to perform the spatial/temporal decomposition of arrays of sensors 118. The present invention may use temporal and spatial filtering to precondition the signals to effectively filter out the common mode characteristics $P_{common\ node}$ and other long wavelength (compared to the sensor spacing) characteristics in the pipe 124 by differencing adjacent sensors 118 and retaining a substantial portion of the stochastic parameter associated with the flow field and any other short wavelength (compared to the sensor spacing) low frequency stochastic parameters. In the case of suitable turbulent eddies 146 (see FIG. 8) being present, the power in the k-ω plane shown in the k-ω plot of FIG. 9 shows a convective ridge 154. The convective ridge 154 represents the concentration of a stochastic parameter that convects with the flow and is a mathematical manifestation of the relationship between the spatial variations and temporal variations described above. Such a plot will indicate a tendency for k-ω pairs to appear more or less along a line 154 with some slope, the slope indicating the flow velocity.

Once the power in the k-ω plane is determined, a convective ridge identifier 158 uses one or another feature extraction method to determine the location and orientation (slope) of any convective ridge 154 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 158 provides information about the different trial convection velocities, information referred to generally as convective ridge information to an analyzer 160. The analyzer 160 then examines the convective ridge information including the convective ridge orientation (slope). Assuming the straight-line dispersion relation given by k=ω/u, the analyzer 160 determines the flow velocity, Mach number and/or volumetric flow, which are output as signals 138. The volumetric flow is determined by multiplying the cross-sectional area of the inside of the pipe 124 with the velocity of the process flow.

The present invention contemplates that the sonar flow meter 116 may be substituted with an ultrasonic flow meter similar to any one of the following types of meters: Transit Time Ultrasonic Flow Meter (TTUF), Doppler Ultrasonic Flowmeter (DUF), and Cross Correlation Ultrasonic Flow Meter (CCUF), similar to that described in the article "Guidelines for the Use of Ultrasonic Non-Invasive Metering Techniques" by M. L. Sanderson and H. Yeung, published on Jul. 17, 2002, which incorporated herein by reference. One such CCUF is GE Panametrics' DigitalFlow™ CTF878 flowmeter which has a pair of ultrasonic sensors disposed axially along the pipe, which is incorporated herein by reference.

It should be appreciated that although in the example shown the pipe 124 is depicted as the gas leg 108 of the gas/liquid separator 102, it is contemplated that the apparatus 112 may be used on any duct, conduit or other form of pipe 124 through which a wet gas 104 may flow.

The method of the invention may be embodied in the form of a computer or controller implemented processes. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. An apparatus for measuring a parameter of a wet gas flow, the apparatus comprising:

a gamma densitometer configured to non-intrusively measure the density of a gas flow traveling through a conduit;

a sonar based flow meter configured to non-intrusively determine a flow rate of the wet gas flow traveling through said conduit; and a processing device communicated with at least one of said gamma densitometer and said sonar based flow meter, wherein said processing device is configured to determine liquid and/or gas flow rates of the wet gas flow using the measured density and flow rate of the wet gas flow.

2. The apparatus of claim 1 wherein said gamma densitometer and said sonar based flow-meter are clamped onto said conduit.

3. The apparatus of claim 1, wherein said sonar based flow meter includes an array of at least three strain-based sensors.

4. The apparatus of claim 1, wherein said sonar based flow meter includes an ultrasonic sonar flow meter.

5. The apparatus of claim 1, wherein said gamma densitometer is disposed in at least one of an upstream location and a downstream location from said sonar based flow meter.

6. A method of measuring a parameter of a wet gas flow, the method comprising:
    non-intrusively determining a mixture density of a wet gas flow traveling through a conduit responsive to changes in radiation transmitted through the wet gas flow;
    non-intrusively determining a flow rate of the wet gas flow traveling through said conduit responsive to the unsteady pressures caused by coherent structures convecting with the wet gas flow; and
    processing said mixture density and said flow rate to determine a flow rate of a liquid phase of the wet gas flow and/or a flow rate of a gas phase of the wet gas flow.

7. The method of claim 6, wherein said step of non-intrusively determining includes non-intrusively determining said mixture density via a gamma densitometer.

8. The method of claim 7, wherein said step of non-intrusively determining includes non-intrusively determining said flow rate via at least one sonar based flow meter.

9. The method of claim 8, wherein said at least one sonar based flow meter is an ultrasonic sonar flow meter.

10. The method of claim 8, wherein prior to said steps of non-intrusively determining a density and non-intrusively determining a volumetric flow rate, said method includes the step of clamping said gamma densitometer and said sonar based flow meter onto said conduit.

11. The method of claim 6, wherein said step of non-intrusively determining includes non-intrusively determining said flow rate using signals from an array of sensors disposed at different axial locations along a length of the pipe, wherein said signals are responsive to said unsteady pressures caused by coherent structures convecting with the gas flow.

12. The method of claim 6 wherein said step of processing includes processing said mixture density and said flow rate of the wet gas flow to determine a flow rate for the liquid and gas phases of the wet gas flow responsive to, $$V_{liq}=V_{sonar}\phi_{liq}, \text{ and}$$

$$V_{gas}=V_{sonar}\phi_{gas}, \text{ where}$$

$V_{liq}$ is the flow rate of the liquid phase of the wet gas flow, $V_{gas}$ is the flow rate of the gas phase of the wet gas flow, $V_{sonar}$ is the flow rate of the wet gas flow, $\phi_{liq}$ is the liquid volume fraction and $\phi_{gas}$ is the gas volume fraction of the wet gas flow.

13. The method of claim 12 wherein said processing includes processing said mixture density ($\rho_{mix}$) to determine liquid hold-up ($\alpha_{liq}$), $\alpha_{liq}$ being related to $\rho_{mix}$ by the relationship, $$\rho_{mix}=\alpha_{liq}\rho_{liq}+\alpha_{gas}\rho_{gas},$$

where $$\alpha_{gas}=1-\alpha_{liq};$$

and where $\rho_{liq}$ is the density of a liquid phase of the wet gas flow, $\alpha_{gas}$ is gas hold-up of the wet gas flow, and $\rho_{gas}$ is the density of the gas phase of the wet gas flow.

14. The method of claim 12 wherein M is determined by the relationship:

$$M=0.79+0.41Fr, \text{ where}$$

Fr is the Froude number and is determined by $$Fr \equiv \left(\sqrt{\frac{\rho_{gas}}{\rho_{liq}-\rho_{gas}}}\right)\frac{V_{Sonar}}{\sqrt{gD}}$$

where $V_{sonar}$ is the flow rate of the wet gas flow, $\rho_{gas}$ is the gas density, $\rho_{liq}$ is the liquid density and gD is the force of gravity multiplied by the inner diameter of the conduit.

15. The method of claim 14 where the liquid volume fraction $\phi_{liq}$ is related to M by the relationship, $$\phi_{liq}=\frac{\alpha_{liq}}{1-M}.$$

16. The method of claim 15 where the liquid volume fraction $\phi_{liq}$ is related to the gas volume fraction $\phi_{gas}$ by the relationship, $$1=\phi_{liq}+\phi_{gas}.$$

17. An apparatus for measuring a parameter of a wet gas flow, the apparatus comprising:
    a first metering device for non-intrusively measuring a mixture density, wherein said first metering device is configured to determine a first characteristic of the wet gas flow, said first characteristic being sensitive to wetness of the wet gas flow;
    a second metering device, wherein said second metering device is configured to non-intrusively determine a second characteristic of the wet gas flow, said second characteristic being relatively insensitive to wetness of the wet gas flow; and
    a processing device communicated with at least one of said first metering device and said second metering device, wherein said processing device is configured to determine the parameter of the wet gas flow using said first and second characteristic.

* * * * *